United States Patent [19]

Tuneberg

[11] Patent Number: 5,267,855
[45] Date of Patent: Dec. 7, 1993

[54] BONDING BASE AND METHOD OF MAKING THE SAME FOR A PLASTIC ORTHODONTIC BRACKET

[75] Inventor: Lee H. Tuneberg, Sheboygan, Wis.

[73] Assignee: American Orthodontics Corporation, Sheboygan, Wis.

[21] Appl. No.: 993,062

[22] Filed: Dec. 18, 1992

[51] Int. Cl.⁵ .............................................. A61C 3/00
[52] U.S. Cl. ....................................................... 433/9
[58] Field of Search ........................................ 433/8, 9

[56] References Cited

U.S. PATENT DOCUMENTS

| | | |
|---|---|---|
| 3,250,003 | 5/1966 | Collito . |
| 3,629,187 | 12/1971 | Waller . |
| 3,745,653 | 7/1973 | Cohl . |
| 3,775,850 | 12/1973 | Northcutt .......................... 433/9 X |
| 4,460,336 | 7/1984 | Smith et al. . |
| 4,838,786 | 6/1989 | Reher et al. ............................ 433/9 |
| 4,927,361 | 5/1990 | Smith et al. ............................ 433/9 |
| 5,071,344 | 12/1991 | Wong et al. ........................... 433/8 |
| 5,108,285 | 4/1992 | Tuneberg . |
| 5,110,290 | 5/1992 | Wong ..................................... 433/9 |
| 5,147,202 | 9/1992 | Masuhara et al. .................. 433/9 X |

*Primary Examiner*—Gene Mancene
*Assistant Examiner*—Nicholas D. Lucchesi
*Attorney, Agent, or Firm*—Lloyd L. Zickert

[57] ABSTRACT

A bonding base and method of making the base for a plastic orthodontic bracket to provide a mechanical lock that inhibits both shear and tensile forces when bonded to a tooth with a mechanical bonding adhesive. The bonding base includes a coating or layer of thermoset epoxy, urethane or acrylate chemistry having partially embedded therein a layer of textured particles that define multi-directional undercuts and projections. The method of making the bonding base includes the steps of applying a substantially uniform in thickness coating of the chosen chemistry to the tooth-attaching side of the bracket, next applying a layer of textured particles to the coating while it is wet, and then curing the coating to lock the textured particles to the bracket for producing a textured mechanical lock.

35 Claims, 1 Drawing Sheet

BONDING BASE AND METHOD OF MAKING THE SAME FOR A PLASTIC ORTHODONTIC BRACKET

This invention relates in general to a bonding base and method for making the base for a plastic orthodontic bracket, and more particularly to a mechanical locking bonding base capable of being bonded to a tooth with a mechanical locking adhesive or bonding material.

BACKGROUND OF THE INVENTION

It is well known in the orthodontic profession that plastic orthodontic brackets are a desirable choice for an orthodontist for orthodontically treating a patient where aesthetics is of paramount interest as plastic brackets can be easily molded of clear or translucent plastic resins that enhance the aesthetics of a bracket system, which are particularly better than that of metal brackets. However, plastic brackets have drawbacks as far as strength characteristics are concerned, and also as far as methodology for bonding the brackets to teeth.

To overcome the strength factor, plastic brackets have been filled with reinforcing substances, such as described in U.S. Pat. Nos. 3,922,787 and 4,107,844, and provided with metal archwire slots, as also shown in U.S. Pat. No. 4,107,844.

With respect to bonding plastic brackets to teeth, primers are first used such as methacrylate-based liquid for softening the tooth-attaching surface of the bracket prior to using "one step" or paste—paste bonding composites. Difficulties in using primers often yield unsatisfactory bonding results. Primers are temperature dependent which yield more or less final bond strength. Primer coating thickness affects bond strength and presently can only be applied at chairside by eyeballing the thickness. Excess primer on the base of the bracket can flow into tie wing areas and inadvertently soften critical areas of the bracket leading to premature bracket failure. Primers are shelf-life sensitive and can lose potency which cannot be detected during use but may be exhibited later in excess bracket bond failure.

Where a plastic bracket includes a strength-reinforcing filler, the filler may diminish the primer reaction sites on the bracket base which ultimately could affect bond strength. Most plastic brackets are pure polycarbonate or glass-filled polycarbonate. While glass-filled polycarbonate brackets produce better strength characteristics in a finished bracket, bonding becomes more difficult with higher filled percentages as the glass filler competes with reaction sites on the base, yielding less bond strength. On the other hand, where less filler is used, a weaker bracket is produced.

As above mentioned, only "one step" or paste—paste bond composites are now generally used for bonding plastic brackets with any degree of reliability. Visible light-cured composites, which are rapidly gaining wide acceptance in the orthodontic field, cannot be effectively used due to extreme variability of bond strength, and/or significantly greater chair time needed for bracket base preparation.

Various base structures have previously been suggested for enhancing the mounting of plastic brackets onto teeth. For example, the bracket in U.S. Pat. No. 3,303,565 shows in one embodiment a curled lip for defining a channel designed to overlie the incisal edge of a tooth.

The bracket in U.S. Pat. No. 3,765,091 shows perforation of the base in the embodiment of FIG. 1 and the use of slots in the embodiment of FIG. 5, and the use of blind openings in the embodiment of FIG. 11. Other types of slotting arrangements have also been used. However, the biggest drawback of heretofore known plastic brackets is the inability to reliably and consistently bond the brackets to the teeth.

SUMMARY OF THE INVENTION

The bonding base and method of making the base according to the present invention permits bonding the plastic brackets to teeth in the identical manner of bonding stainless steel brackets to teeth including the use of light-cured bonding composites. Moreover, the present invention allows the manufacturer to "prepaste" brackets with adhesive, thereby saving the orthodontists from engaging in chairside time-consuming preparatory procedures. The use of chairside primers is eliminated by the present invention and all of the problems associated with primer use. Moreover, the present invention permits the use of brackets made of highly filled plastics or different hybrid plastic materials, thereby yielding a much stronger bracket than heretofore possible. Additionally, the bonding base of the present invention constitutes a true mechanical lock for using mechanical bonding materials, thereby eliminating the use of present chemical bonding materials.

Even though many plastic brackets presently being marketed contain grooves or indents on the bracket base for enhancing adhesive retention and bonding, they only serve to generally withstand shear forces. Inasmuch as it is usually necessary to apply forces to a tooth in a three-dimensional plane in order to obtain correction, present bonding techniques depend upon a chemical bond to increase bond strength in a tensile direction. The bonding base of the present invention increases bonding strength in a plastic bracket in both shear and tensile modes.

The bonding base of the present invention includes a layer of one of the following chemistries: 1) epoxy 2) urethane 3) acrylate (light-cure) With thermoset epoxy resins, the molecules contain one or more rings commonly defined as ethylene oxide

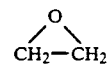

Other variations include trimethylene oxide

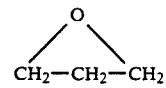

or tetrahydrafuran

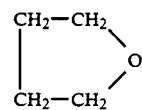

The epoxies are cured with either basic or acidic agents, examples of which include:
  Basic: primary amines; secondary amines; inorganic bases; Lewis bases; amides.
  Acidic: anhydrides; phenols; Lewis acids.

With thermoset urethane resins, the primary molecule is the isocyanate group represented as —N═C═O. Isocynates will proceed in reaction with compounds containing active hydrogens, examples of which include: amines; polyols; urea; other urethanes.

With acrylate resin systems, a reactive acrylate-methacrylate, for example

can be added to the epoxy or urethane backbone. A photoinitiator is required and, when exposed to the proper wavelength, cures via a free radical mechanism. These photoinitiators may be activated by visible or UV light spectrums.

All of the above coatings systems and chemistries are well known to those skilled in the resin-coating chemical arts.

While bonding base coatings of the above three systems have all given satisfactory results on plastic brackets based on in vitro testing, the thermoset urethane system has consistently given the best results and will be detailed further.

The bonding base also includes a layer of textured particles partially embedded in the bonding layer. The particles of the textured layer define undercuts and projections for a mechanical lock. The bonding layer is applied in an uncured or wet state to the tooth-attaching side of the bracket base in a uniform manner so that the thickness is substantially uniform over the tooth-attaching surface. While the bonding layer is wet or in a non-cured state, a layer of textured particles is applied thereto. These particles are capable of defining multi-directional undercuts and projections. Thereafter, the bonding layer is suitably cured. Both the bonding layer (whether an epoxy, urethane or acrylate) and the particles are inert to the bonding adhesives whereby a true mechanical lock is formed capable of being bonded to a tooth with the standard mechanical lock adhesives including the light-curable adhesives.

It is therefore an object of the present invention to provide a plastic bracket with a new and improved bonding base and method of making same which is capable of bonding to a tooth with a mechanical lock bonding material.

A further object of the present invention is to provide a true mechanical lock base for a plastic bracket that eliminates the need to use a primer in the bonding procedure and which permits the use of a mechanical lock bonding material to produce a strong bond withstanding both shear and tensile forces.

A still further object of the present invention is in the provision of a new and improved bonding base for a plastic bracket and in a method for making the base which includes the steps of applying a coating of a bonding layer to the base followed by a layer of textured particles while the bonding layer is wet (uncured) wherein the particles define multi-directional undercuts and projections. The bonding layer is preferably selected from the group consisting of an epoxy resin, a urethane resin and an acrylate resin, initially applied in the wet or uncured state, whereafter the textured particles are applied and the bonding layer resin then cured to lock the two layers as one.

Another object of the present invention is in the provision of a new and improved mechanical lock on the tooth-attaching side of a plastic bracket which eliminates the need to use a primer in the bonding procedure and permits the use of highly filled plastics or hybrid plastics, thereby producing a stronger bracket which also allows downsizing of the bracket to enhance comfort and hygiene as well as aesthetics.

A further object of the present invention is in the provision of a new and improved bonding base for a plastic bracket which permits the use of light-cured bonding adhesives and also permits a manufacturer to prepaste the brackets with adhesive at the factory.

Another object of the present invention is in the provision of a new and improved bonding base and method for making the base which defines a mechanical lock and permits the bonding of the bracket to a tooth in the same manner as when bonding stainless steel brackets to teeth.

Other objects, features and advantages of the invention will be apparent from the following detailed disclosure, taken in conjunction with the accompanying sheet of drawings, wherein like reference numerals refer to like parts.

DESCRIPTION OF THE INVENTION

Figure 2:
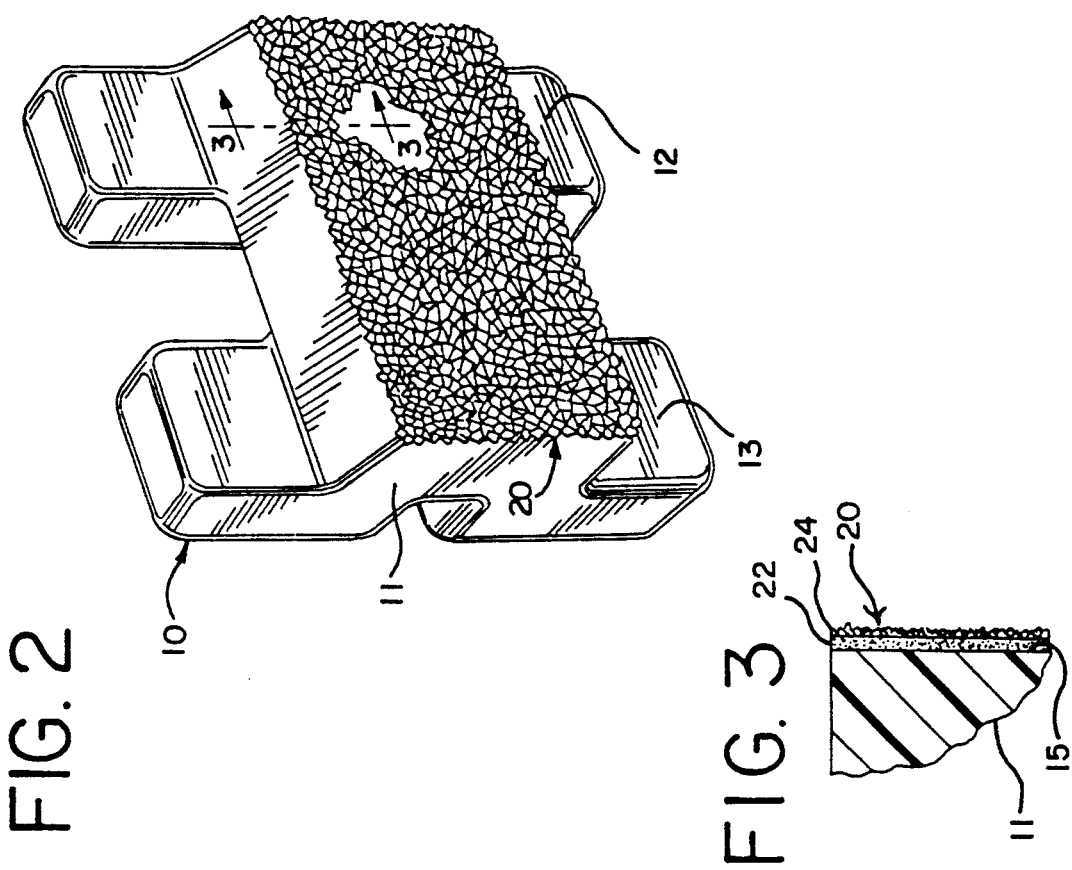
FIG. 2 is a rear perspective view of the bracket of FIG. 1.
Figure 3:
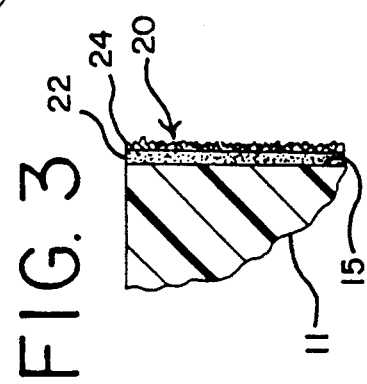
FIG. 3 is a greatly enlarged fragmentary sectional view taken substantially along line 3—3 of FIG. 2.
Figure 1:
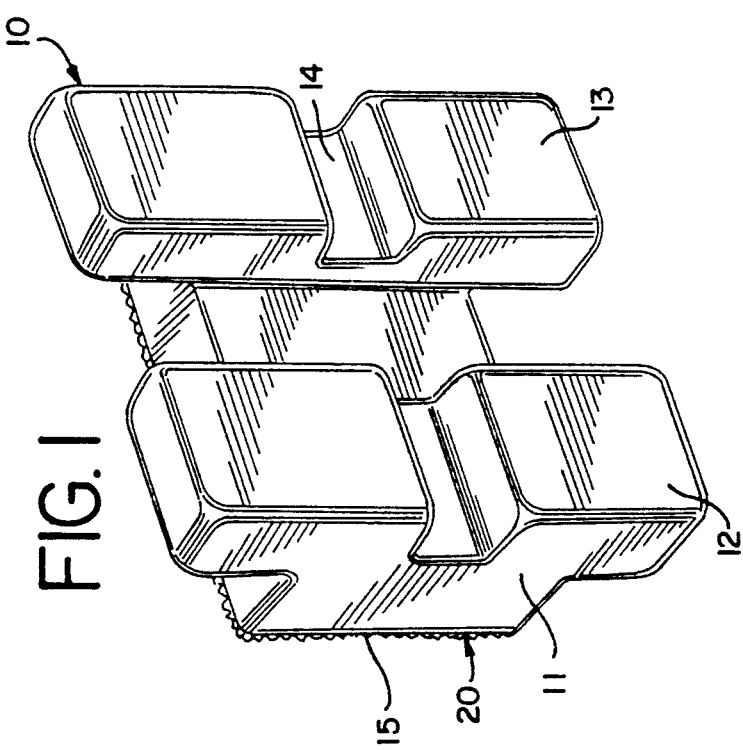
FIG. 1 is a front perspective view of a plastic bracket having a mechanical lock base according to the present invention.

The bonding base of the invention provides a mechanical lock for plastic brackets of the usual polycarbonate type or other suitable type, filled or unfilled, which provides a mechanical retention base for bonding the bracket to a tooth surface with well known mechanical bonding materials or adhesives long used for bonding metal brackets to teeth. Thus, the bonding base of the present invention will produce a bond strength between a bracket and a tooth that is substantially the same as that produced between a stainless steel bracket having a foil mesh base and a tooth without impairing the strength of the bracket. Further, by eliminating the need to use a primer, the multitude of problems heretofore encountered in using primers on plastic brackets is eliminated. By providing a true mechanical lock for the base of a plastic bracket, the bond between the tooth and the bracket will withstand both shear and tensile forces, thereby enhancing the life of the bond.

The method of making the mechanical lock for a plastic bracket according to the invention includes the application of a coating (bonding layer) of an epoxy resin, a urethane resin or a multifunctional acrylated resin to the tooth-attaching surface or side of a plastic bracket and, while uncured, applying thereto a layer of textured particles partially embedded in the bonding layer resulting in a coating consisting of the cured resin as a matrix in which the textured particles are firmly anchored. The coating thus achieved shields the plastic material of the bracket from the bonding adhesive and permanently locks the particles to the bracket. The textured particles are such that they produce a multiplicity of undercuts and projections into and around which the bonding adhesive flows during the bonding procedure. The mechanical lock bonding base is inert to the bonding adhesives.

The bracket plastic material may be filled or unfilled polycarbonate, or a hybrid plastic material. The filler may be glass or any other suitable material that would enhance the reinforcing of the plastic material so that the bracket has increased strength.

The bonding layer resin will preferably be clear or translucent, that is, to allow the transmission of visible light energy. In the uncured state, the bonding layer resin should have sufficient viscosity so that it can be applied in a thin film and yet not slump or pool on curvate surfaces, thereby providing a substantially uniform thickness throughout. Further, the bonding layer resin should preferably be abrasion-resistant with a high toughness characteristic and have a low shrinkage factor and a low moisture sorption factor. Preferably, shrinkage of the bonding layer resin should not exceed one to two percent, and moisture sorption should not exceed one to two percent. Further, the resin will be of a type that will bind to the plastic bracket and any filler. Also, the bonding layer resin should exhibit minimal elongation, but not be brittle, and have a high hardness factor. This layer may be rolled, brushed or sprayed onto the tooth-attaching side of the plastic bracket.

The texturing particles or substance should preferably be of a mesh size that permits maximum adhesion into the coating, while minimizing the overall facio-lingual height of the bracket. The particles preferably should be irregularly shaped to provide multi-directional undercuts and projections and have the ability to be surface treated or primed to maximize the interconnection with the coating without adversely affecting its mechanical locking ability to a bonding adhesive. For example, the particles may be coated with the same uncured chemistry, but of a lower viscosity. Alternately, the particles may be coated with a variety of organosilanes that have been properly hydrolyzed. Other treating processes include physical encapsulation of the filler with similar coating chemistry. The particles preferably should have a translucency or ability to transmit at least some of the visible light energy to allow the reflection and refraction of light similar to that of a natural tooth. Additionally, the texturing particles should have a range of MOHS hardness to be suitable for different clinical applications including a hardness less than tooth enamel. The textured particles may be pressed, blown or sprayed onto the epoxy film or coating and may be of the type disclosed in U.S. Pat. No. 5,108,285. More particularly, the particles may be sharp multi-edged shards of highly purified aluminum oxide with a minimum density of 3.9 grams per cc. The aluminum oxide is preferably 99.5 percent pure and 220 mesh size.

The electrically fused high purity alumina, a polycrystalline ceramic, made from the Bayer process for the texturing surface is carefully sieved in the proper mesh size for use as it has been determined that particles larger or smaller than about 220 mesh size do not provide a proper mechanical retention or mechanical lock with a dental composite adhesive resin. Any suitable mechanical adhesive can be used to bond the bracket with the base of the present invention to a tooth. Suitable adhesives include the Bis-GMA bonding composites, such as No-Mix 30 or Force II sold by American Orthodontics Corporation of Sheboygan, Wis.

A typical composition of the fused alumina (MOHS hardness 9.0) is as follows:

| | |
|---|---|
| $Al_2O_3$ | 99.55% |
| $TiO_2$ | .01% |
| $SiO_2$ | .05% |
| $CaO$ | .03% |
| $MgO$ | .02% |
| $Na_2O$ | .14% |
| $Fe_2O_3$ | .04% |

Another form of textured particles could be comprised as follows:

| | | | MOHS Hardness |
|---|---|---|---|
| Filler "1" | $Al_2O_3$ | 40–50% | 8.0–9.0 |
| | $SiO_2$ | 35–45% | |
| | $CaO$ | 15–25% | |
| Filler "2" | $SiO_2$ | 55–70% | 3.5–5.5 |
| | $Al_2O_3$ | 25–35% | |
| | $CaO$ | 15–25% | |
| Filler "3" | $SiO_2$ | 50–60% | 4.0–5.0 |
| | $CaO$ | 30–40% | |
| | $MgO$ | 1–5% | |

All fillers were finer than 180 mesh size.

Because of the base of the present invention constitutes a true mechanical lock textured base, or one with multi-directional undercuts and projections, which permits the use of stronger composite plastic materials for the bracket substrate, the bracket profile may be made smaller in all dimensions, thereby enhancing patient aesthetics, hygiene and comfort and avoiding occlusal traumas.

A typical twin edgewise plastic bracket is illustrated in the drawings and generally indicated by the numeral 10. The bracket generally includes a base 11 and tie wing sets 12 and 13, each of which includes upper and lower tie wings. A horizontally extending and labiobuccally opening archwire slot 14 is formed between the tie wings for receiving an archwire of the usual type that may be ligated to the bracket. The base 11 includes a tooth-attaching side or surface 15 onto which is formed a mechanical lock means 20 in accordance with the invention. As above mentioned, the mechanical lock means 20 includes multi-directional undercuts and projections to coact with an adhesive in bonding the bracket to a tooth.

The mechanical lock means 20 includes a layer or coating of epoxy resin, urethane or multifunctional acrylated resin 22 on the tooth-attaching side 15 of the bracket and a layer of textured particles 24 partially embedded in the layer. The method of making the mechanical lock means 20 includes the application of a coating of one of the aforementioned chemistries and then applying a layer of textured particles to the coating while it is uncured. Thereafter, the coating is suitably cured to define the mechanical lock means 20.

While the mechanical lock base is illustrated with a twin edgewise orthodontic bracket, it should be appreciated it could be used on any type of plastic bracket, including single-width edgewise or light-wire brackets.

EXAMPLE I

A group of 20% glass-filled polycarbonate brackets, such as those sold by American Orthodontics Corporation, was fixtured in an aluminum tray such that the bracket bases were facing upward. A two-part polyol-cured polyurethane (APTEK #XB3675; Aptek, Inc., Valencia, Calif.) was vacuum spatulated to mix the components and to prepare for spray-coating the urethane onto the tooth-attaching surfaces of the bracket bases. American Orthodontics SILKON maxillary central brackets were used. The brackets in the tray were placed on a conveyer belt and conveyed under a Binks Model 115 spray gun operated with an air pressure of 50 PSI. The conveyer speed was approximately 2.5 inches per second. This produced a spray coating thickness of approximately 0.002 inches. While the urethane was wet, various fillers (textured particles) were blown onto the urethane film and inspected for mono-layer thickness. The urethane was allowed to gel for four hours at 25° C. Thereafter, the brackets were placed in an air oven set at 110° C. for four hours to cure and crosslink the urethane.

Physical specs of APTEK #XB3675 polyol-cured urethane 1) mixed viscosity: 3000 cps (approximately) (can be made more thixotropic, if desired)

2) Linear shrinkage: <1.5%

3) $H_2O$ sorption: <1.5% (2-hour water boil)

4) Hardness: approximately 80 shore D (can range from 60-95 Shore D)

5) Tensile strength: approximately 10,000 PSI (range from 5000-20,000 PSI)

6) Elongation: approximately 12% (range from 1%-30%)

7) Color: clear to very translucent

The mechanical lock base on the brackets was then subjected to bond tests utilizing bovine teeth. The teeth were fixtured in acrylic and the facial surfaces were prepared using conventional techniques. Three different types of accepted bonding adhesive systems were used for bonding the brackets to the bovine teeth. These systems included American Orthodontics "NO-MIX:30" "one step", 3M "CONCISE" paste—paste, and American Orthodontics "SPECTRUM LT. CURE" visible light cure. The shear forces were applied by an Instron Model 1000 testing machine having a crosshead speed of 0.5 inches per minute, a 100 pound load cell set at the 50 pound range, and the machine set in the break mode so that as soon as the bracket breaks away from the tooth the machine stops. A 0.014 inch stainless steel ligature twisted into a braid to provide double thickness was trained over the tie wings of the bracket and connected to the crosshead of the testing machine to apply an occlusally directed shear force on the bracket. As compared to traditional primer based chemical bond plastic brackets, the following results were observed where debonding was measured in pounds of shear.

| Mechanical Lock Base | | | | | Bonding Composite Used | Traditional Chemical Bond with Primer |
|---|---|---|---|---|---|---|
| Fused Alumina | | | | | | |
| 220 grit | 180 grit | Filler 1 | Filler 2 | Filler 3 | | |
| 19.5 | 17.1 | 26 | 27.3 | 28.4 | American Orthodontics "NO-MIX:30" | 16 |
| 22.2 | 23.0 | 28.0 | 29.1 | 29.7 | 3M "CONCISE" | 20.4 |
| 25.3 | 22.0 | 29.5 | 29.3 | 36.0 | American Orthodontics "SPECTRUM LT. CURE" | <10 |

EXAMPLE II

Same as Example I, but air pressure was 38 PSI, coating was a two-part epoxy anhydride (APTEK CF 4300) and the cure was 120° C. for eight hours. The following shear values in pounds were recorded.

| Mechanical Lock Base | | | | Bonding Composite Used | Traditional Chemical Bond with Primer |
|---|---|---|---|---|---|
| 220 grit | Filler 1 | Filler 2 | Filler 3 | | |
| 16.4 | 19.6 | 24.3 | 20.4 | American Orthodontics "NO-MIX:30" | 16 |
| 21.3 | 18.0 | 21.5 | 23.3 | American Orthodontics "SPECTRUM" LT. CURE | <10 |

EXAMPLE III

Same as Example I, except:

One part multifunctional acrylate (light cure) was used (Master Bond UV15-7; Master Bond, Inc., Hackensack, N.J.).

Brackets were placed "base up" in an aluminum tray and brushed with the uncured acrylate with a resin thickness of <0.002".

While the acrylate coating was wet, various fillers were pressed into the surface and inspected for monolayer thickness.

The multifunctional acrylate coating was then cured under a UV light source at 200 watts per linear inch at a conveyer speed of five feet per minute in air atmosphere.

The following shear values in pounds were recorded:

| Mechanical Lock Base | | | | Bonding Composite Used | Traditional Chemical Bond with Primer |
|---|---|---|---|---|---|
| 220 grit | Filler 1 | Filler 2 | Filler 3 | | |
| 17.0 | 22.0 | 19.7 | 21.4 | American Orthodontics "NO-MIX:30" | 16 |
| 19.0 | 21.2 | 22.0 | 24.6 | American Orthodontics "SPECTRUM" LT. CURE | <10 |

It will be appreciated that the main chemistry tested has been of the urethane variety. While all chemistries—urethane, epoxy and acrylates—have been found to give increased bond strength to plastic brackets and the elimination of chairside primer use the urethane films have the advantage of increased flexibility and elongation without any loss of chemical resistance, impact resistance, thermal cycling failure, or stress-crack resistance.

In view of the foregoing, it will be appreciated that the mechanical lock base of the present invention for a plastic bracket and the means for making the base provides a plastic bracket having mechanical retention ability for use with mechanical adhesives to bond to teeth to provide a bond strength substantially equal to that heretofore known in bonding metal brackets to teeth. The bond will withstand both shear and tension forces.

It will be understood that while the preferred resin for the bonding layer is a urethane, modifications and variations may be effected without departing from the scope of the novel concepts of the present invention, but it is understood that this application is to be limited only by the scope of the appended claims.

I claim:

1. A method of making a mechanical lock means for the tooth-attaching side of a plastic orthodontic bracket so the bracket may be mechanically bonded to a tooth with a mechanical bonding adhesive to withstand tensile and shear forces, which method comprises the steps of applying to the tooth-attaching side of the bracket a bonding layer selected from the group consisting of an uncured epoxy resin, an uncured urethane resin, and an uncured acrylate resin, applying a layer of textured particles to the bonding layer while it is uncured which produces a multiplicity of undercuts and projections, and curing the bonding layer thereby locking the textured particles to the bracket for producing a textured mechanical lock.

2. The method of claim 1, wherein the plastic bracket is polycarbonate.

3. The method of claim 1, wherein the plastic bracket is plastic having a low moisture absorption and high tensile strength.

4. The method of claim 1, wherein the step of applying the uncured bonding layer resin includes the step of spraying the resin onto the bracket.

5. The method of claim 1, wherein the step of applying the uncured bonding layer resin includes the step of brushing the resin onto the bracket.

6. The method of claim 1, wherein the step of applying the uncured bonding layer resin includes the step of rolling the resin onto the bracket.

7. The method of claim 1, wherein the textured particles is fused alimina.

8. The method of claim 7, wherein the fused alumina is approximately 200 grit size.

9. The method of claim 8, wherein the mesh size of the particles is such as to produce maximum adhesion into the cured bonding layer resin and maximum locking ability for a bonding adhesive.

10. The method of claim 8, wherein the mesh size of the particles is such as to produce maximum adhesion into the cured bonding layer resin while minimizing the overall facio-lingual height of the bracket.

11. The method of claim 8, wherein the particles have a translucency such as to reflect and refract visible light energy similar to a natural tooth.

12. The method of claim 1, wherein the textured particles having MOHS hardness in the range of about 3.5 to 9.0.

13. The method of claim 1, wherein the textured particles is fused silica.

14. The method of claim 1, wherein the textured particles are irregularly shaped.

15. The method of claim 1, wherein the textured mechanical lock permits use of stronger plastic materials for the bracket such that the bracket may be made smaller thereby enhancing patient aesthetics, hygiene, and comfort, and avoiding occlusal traumas.

16. The method of claim 1, wherein the step of applying the textured particles includes the step of pressing the particles onto the uncured bonding layer resin.

17. The method of claim 1, wherein the step of applying the textured particles includes the step of blowing the particles onto the uncured bonding layer resin.

18. The method of claim 1, wherein the step of applying the textured particles includes the step of spraying the particles onto the uncured bonding layer resin.

19. The method of claim 1, wherein the bonding layer resin will transmit visible light.

20. The method of claim 1, wherein the bonding layer resin has a viscosity such that it can be applied in a thin film.

21. The method of claim 1, wherein the bonding layer resin has a viscosity such that it will not slump or pool on a curvate surface.

22. The method of claim 1, wherein the bonding layer resin exhibits abrasion resistance and high toughness.

23. The method of claim 1, wherein the bonding layer resin exhibits minimum elongation with high hardness.

24. The method of claim 1, wherein the bonding layer resin has minimal shrinkage.

25. The method of claim 1, wherein the bonding layer resin has minimal moisture sorption.

26. The method of claim 1, wherein the bonding layer resin is polyurethane and the step of curing includes allowing the resin to gel and subjecting the bracket and lock means to a temperature to cure and crosslink the resin.

27. The method of claim 26, wherein the step of curing the adhesive includes allowing the resin to gel for four hours at 25° C. and subjecting the bracket and lock means to a temperature of about 110° C. for four hours to cure and crosslink the resin.

28. A mechanical bond lock means for a plastic orthodontic bracket made according to the method of claim 1.

29. An orthodontic plastic bracket having a mechanical lock on its tooth-attaching side, which mechanical lock comprises a layer of a bonding resin against its attaching side, and a layer of textured substance partially embedded in the bonding layer, said textured substance being such as to produce a multiplicity of undercuts and projections capable of coacting with a mechanical bonding material to bond the bracket to a tooth, whereby a mechanical bond is formed that resists both tensile and shear forces.

30. An orthodontic plastic bracket according to claim 29, in which the resin is a polyol-cured urethane.

31. An orthodontic plastic bracket according to claim 29, in which the resin is an epoxy.

32. An orthodontic plastic bracket according to claim 29, in which the resin is an acrylate.

33. An orthodontic plastic bracket as defined in claim 29, wherein the textured substance is fused alumina.

34. An orthodontic plastic bracket as defined in claim 29, wherein the textured substance has a MOHS hardness in the range of about 3.5 to 9.0.

35. An orthodontic plastic bracket as defined in claim 29, wherein the textured substance has a MOHS hardness less than tooth enamel.

* * * * *